(12) United States Patent
Basset et al.

(10) Patent No.: US 7,473,814 B2
(45) Date of Patent: Jan. 6, 2009

(54) PROCESS FOR CONVERTING METHANE INTO ETHANE

(75) Inventors: Jean-Marie Basset, Caluire (FR); Philippe Bres, Marq en Bareul (FR); Christophe Coperet, Lyons (FR); Barry Martin Maunders, Surrey (GB); Daravong Soulivong, Lyons (FR); Mostafa Taoufik, Rillieux-la-Pape (FR); Jean Thivolle-Cazat, Fontaines-sur-Saone (FR)

(73) Assignee: BP Chemicals Limited, Middlesex (GB)

( * ) Notice: Subject to any disclaimer, the term of this patent is extended or adjusted under 35 U.S.C. 154(b) by 521 days.

(21) Appl. No.: 10/517,212

(22) PCT Filed: Jun. 4, 2003

(86) PCT No.: PCT/GB03/02426

§ 371 (c)(1),
(2), (4) Date: Dec. 8, 2004

(87) PCT Pub. No.: WO03/104171

PCT Pub. Date: Dec. 18, 2003

(65) Prior Publication Data

US 2005/0272966 A1    Dec. 8, 2005

(30) Foreign Application Priority Data

Jun. 10, 2002  (FR) .................................. 02 07066

(51) Int. Cl.
*C07C 2/00* (2006.01)

(52) U.S. Cl. ........................................ 585/700; 585/943

(58) Field of Classification Search ................ 585/700, 585/943

See application file for complete search history.

(56) References Cited

U.S. PATENT DOCUMENTS

| | | | | |
|---|---|---|---|---|
| 4,199,533 A * | 4/1980 | Benson | ........................ | 585/500 |
| 4,450,310 A * | 5/1984 | Fox et al. | .................... | 585/400 |
| 4,467,047 A * | 8/1984 | Johnson | ...................... | 502/246 |
| 4,467,130 A * | 8/1984 | Olah | .......................... | 585/709 |
| 4,956,327 A * | 9/1990 | Erekson et al. | ............. | 502/216 |
| 5,093,542 A * | 3/1992 | Gaffney | ...................... | 585/500 |
| 5,146,027 A * | 9/1992 | Gaffney | ...................... | 585/500 |
| 5,328,575 A * | 7/1994 | Geiger | .................. | 204/157.15 |
| 5,406,017 A * | 4/1995 | Withers, Jr. | .................. | 585/500 |
| 5,414,176 A | 5/1995 | Amariglio et al. | | |
| 5,959,170 A * | 9/1999 | Withers, Jr. | .................. | 585/500 |
| 6,229,060 B1 * | 5/2001 | Vidal et al. | .................. | 585/708 |
| 6,281,160 B1 * | 8/2001 | Basset et al. | ................. | 502/332 |
| 6,469,225 B1 * | 10/2002 | Basset et al. | ................ | 585/708 |
| 6,727,397 B2 * | 4/2004 | Basset et al. | ................ | 585/708 |
| 6,756,339 B1 * | 6/2004 | Rokicki et al. | .............. | 502/304 |
| 2003/0045765 A1 * | 3/2003 | Basset et al. | ................ | 585/700 |

FOREIGN PATENT DOCUMENTS

DE    31 16 409 A1    11/1982
WO    WO 01/04077 A1 *    1/2001

OTHER PUBLICATIONS

Li, Lin, Borry, Richard W., Iglesia, Enrique. Reaction-transport simulations of non-oxidative methane conversation with continuous hydrogen removal—homogenerous-heterogenous reaction pathways. Chemical Engineering Science 56 (2001) 1869-1881.*

Zhang, Jun-qi, Yang, Yong-jin, Zhang, Jin-song, Liu, Qiang, Tan, Ke-rong. Non-Oxidative Coupling of Methane to C2 Hydrocarbons under Above-Atmospheric Pressure Using Poulsed Microwave Plasma. Energy & Fuels 2002, 16 687-693.*

* cited by examiner

*Primary Examiner*—Walter D Griffin
*Assistant Examiner*—Huy-Tram Nguyen
(74) *Attorney, Agent, or Firm*—Finnegan, Henderson, Farabow, Garrett & Dunner, L.L.P.

(57) ABSTRACT

The invention relates to a process for producing ethane comprising contacting methane with a metal catalyst selected from metal hydrides, metal organic compounds and mixtures thereof. It also relates to a process for the conversion of methane to carbon-containing products comprising contacting methane with a metal catalyst comprising at least one metal, Me, chosen from the lanthanides, the actinides and the metals from Groups 2 to 12 of the Periodic Table of the Elements, so as to produce ethane in a proportion of at least 65%, especially at least 98% or 99% by weight with respect to carbon-containing products formed in the process. The process can be a single-step process, preferably carried out under conditions involving a non-oxidative catalytic coupling of methane, in particular under operating conditions maintained substantially constant, preferably continuously, during the ethane production, e.g. at a temperature ranging from −30° C. to +80° C., preferably from 20° C. to 500° C., under a total absolute pressure ranging from $10^{-3}$ to 100 MPa, preferably from 0.1 to 50 MPa. The metal catalyst may be chosen from metal catalysts supported on and preferably grafted to a solid support. One of the main advantages of the present invention is to produce ethane with a very high selectivity.

19 Claims, No Drawings

PROCESS FOR CONVERTING METHANE INTO ETHANE

The present invention relates to a process for producing ethane from methane and to a process for the conversion of methane to ethane.

Alkanes and in particular methane are products which are generally difficult to employ in reactions because of their high chemical inertia, and are used essentially as fuels and energetic materials. Furthermore, methane, which is the main constituent of natural gas, is one of the most widespread sources of hydrocarbons in the world.

There are two main routes for converting methane: an indirect route involves the intermediacy of a mixture of carbon monoxide and hydrogen, also known as "synthesis gas", and makes it possible to convert methane to liquid fuels or other chemicals, and a direct route converts methane to methanol or to hydrocarbons, in particular to $C_2$ hydrocarbons. Most industrial processes for the conversion of methane use the indirect route and thus convert methane to "synthesis gas" by steam reforming and subsequently synthesize methanol or petrols using "synthesis gas" as intermediate. However, these processes require a great deal of energy and very high temperatures ranging beyond 800° C.

To avoid these difficulties, numerous studies have been carried out for the purpose of developing processes for the conversion of methane by the direct route. Mention may be made, among these processes, of oxidative coupling, thermal coupling, plasma coupling and non-oxidative catalytic coupling.

In particular, the oxidative coupling of methane consists in converting methane directly to ethane and to ethylene in the presence of oxygen and of a catalyst, and in then converting these hydrocarbons to liquid hydrocarbon fuels, such as petrols. However, the process by oxidative coupling generally results in the formation of relatively large amounts of by-products, such as carbon monoxide and carbon dioxide, and has to be carried out at high temperatures, in particular greater than 600° C.

Thermal coupling makes it possible to convert methane directly to $C_2$ hydrocarbons at very high temperature. However, in addition to ethane, large amounts of ethylene and acetylene are formed, which products often constitute the major products formed by the reaction. In addition, the thermal coupling process is carried out at extremely high temperatures, generally of greater than 1200° C.

Plasma coupling consists of activating methane to methyl radicals by virtue of the very high energy provided by the plasma and in forming in particular ethane, propane, ethylene, acetylene and even small amounts of $C_4$ hydrocarbons. Although this process can exhibit a high selectivity for ethane under certain conditions, in particular in the presence of glass or alumina beads (Korean J. Chem. Eng., 18(2), 196-201 (2001)), it requires the use of high energy and does not appear to be very attractive from the viewpoint of industrial application.

It is known (J. Phys. Chem. A, Vol. 103, No. 22, 1999, 4332-4340) to carry out a catalytic oligomerization of methane by heating under microwaves in the presence of a catalyst chosen from nickel or iron powders or from activated carbons. By virtue of the energy of the microwaves as source of activation, this process makes it possible to form a mixture of $C_2$ to $C_8$ hydrocarbons, in particular $C_2$ to $C_6$ hydrocarbons, for example a mixture of ethane, ethylene, acetylene and benzene, and also carbon monoxide and carbon dioxide. The formation of carbon oxides appears to show that this process is an oxidative coupling method. In addition, this process is not sufficiently selective to form solely light alkanes and in particular ethane.

It is also known (Chem. Commun., 1999, 943-944) to carry out, at 450° C., selective activation of methane to alkenes in the presence of a hydrogen accumulation system comprising titanium and 0.4% by weight of nickel. Methane is converted to $C_2$ to $C_4$ alkenes and alkanes, the alkenes and in particular ethylene constituting the major products formed. However, the activation of methane carried out under these conditions is not sufficiently selective to form essentially light alkanes and in particular ethane.

U.S. Pat. No. 5,414,176 discloses a process for converting methane to higher hydrocarbons, in particular to $C_2$ to $C_7$ hydrocarbons. The process successively comprises bringing a gas stream consisting essentially of methane into contact with a catalyst comprising a transition metal dispersed over a support based on refractory oxide, then bringing the catalyst into contact with a stream of hydrogen, so as to form a gas mixture of higher hydrocarbons and of hydrogen, subsequently recovering the gas mixture, and separating the higher hydrocarbons from the hydrogen. However, the conversion of methane is not very selective, since it results in the formation of a mixture of hydrocarbons ranging from $C_2$ to $C_7$. Furthermore, the process is relatively complex, since it comprises a sequence of several stages, in particular two successive contacting operations of the catalyst.

German Patent Application DE 31 16 409 discloses a process for producing higher hydrocarbons, in particular for producing $C_2$ hydrocarbons (essentially ethane, ethylene and acetylene) from methane. The process comprises (i) a first stage for a dissociative chemisorption of methane on a catalyst surface (e.g. a platinum catalyst) at a temperature of 180 to 300° C., (ii) a second stage for cooling the chemisorbed intermediate products at a temperature of 120 to 150° C. so as to form higher hydrocarbons by a C—C recombination, and (iii) a third stage for desorbing the higher hydrocarbons with a stream of hydrogen. The German Patent Application is silent about the ethane production compared with the formation of the other higher hydrocarbons. In addition, it discloses a multi-stage process carried out at different temperatures and involving the use of hydrogen in the last stage for producing the higher hydrocarbons.

The present invention relates to a process for producing ethane from methane, in particular to a process for converting methane essentially into ethane, the process being advantageously carried out with a very high selectivity by weight for ethane with respect to carbon-containing products formed. It is considered that the selectivity by weight for ethane is generally at least 65%, preferably at least 70%, in particular at least 80%, especially at least 90%, and more especially at least 95%. The term "selectivity by weight for ethane" is generally understood to mean the part by weight of ethane formed per 100 parts by weight of carbon-containing products formed in the process. In particular, it is noted that ethane can thus be formed directly with a very high degree of purity, for example with a selectivity by weight of at least 98% or even of at least 99%.

The process of present invention can, in addition, advantageously be carried out without forming detectable amounts of carbon-containing products other than alkanes, for example of alkenes (e.g. ethylene), of alkynes (e.g. acetylene), of aromatic compounds (e.g. benzene), of carbon monoxide and/or of carbon dioxide.

Furthermore, the process of the present invention can be advantageously carried out under conditions involving a non-oxidative catalytic coupling of methane. Preferably, it is a single-stage process, in particular carried out under operating conditions maintained substantially constant, preferably continuously, during the ethane production.

The Periodic Table of the Elements mentioned below is that proposed by the IUPAC in 1991 and which is found, for example, in "CRC Handbook of Chemistry and Physics", 76th Edition (1995-1996), by David R. Lide, published by CRC Press Inc. (USA).

A first subject-matter of the invention is a process for producing ethane, characterized in that it comprises bringing methane into contact with a metal catalyst chosen from metal hydrides, metal organic compounds and mixtures thereof. The metal catalyst preferably comprises at least one metal, Me, chosen from the lanthanides, the actinides and the metals from Groups 2 to 12, preferably 3 to 12, of the Periodic Table of the Elements.

A second subject-matter of the invention is a process for the conversion of methane to carbon-containing products, characterized in that methane is brought into contact with a metal catalyst comprising at least one metal, Me, chosen from the lanthanides, the actinides and the metals from Groups 2 to 12, preferably 3 to 12, of the Periodic Table of the Elements, so as to produce ethane in a proportion of at least 65% by weight with respect to carbon-containing products formed in the process.

In the present description, the process of the invention generally means the process for producing ethane as well as the process for the conversion of methane.

In the process of the invention, methane reacts essentially with itself. This is generally known as the methane coupling reaction or alternatively methane homologation reaction. The reaction results essentially from bringing methane into contact with a metal catalyst and generally leads to the formation, in particular by a reversible reaction, of ethane and hydrogen, especially according to the following equation:

$$2CH_4 \rightarrow C_2H_6 + H_2 \tag{1}$$

The process of the invention can be carried out by bringing methane into contact with a metal catalyst under a total absolute pressure ranging from $10^{-3}$ to 100 MPa, preferably from 0.1 to 50 MPa, in particular from 0.1 to 30 MPa or from 0.1 to 20 MPa, especially from 0.1 to 10 MPa.

The process of the invention can be also carried out at a temperature ranging from −30 to +800° C., preferably from 0 to 600° C., in particular from 20 to 500° C. and especially from 50 to 450° C., for example from 50 to 400° C. or from 50 to 350° C. The most preferred range of the temperature is from 200 to 600° C., and especially from 250 to 500° C.

The process of the invention can be carried out in various ways, for example by adding the methane to the metal catalyst, or by adding the metal catalyst to the methane, or by simultaneously mixing the methane and the metal catalyst.

Generally, the methane used in the present invention constitutes essentially the only initial alkane used in the conversion. However, the process of the invention can be carried out by contacting methane with the metal catalyst in the presence one or more other initial alkane(s), such as those present in natural gas. The other optional initial alkane(s) can be chosen from $C_2$ to $C_{30}$ alkanes, preferably $C_2$ to $C_{20}$ alkanes, in particular $C_2$ to $C_{12}$ or $C_2$ to $C_{10}$ alkanes, especially from propane, n-butane, isobutane, n-pentane, isopentane, n-hexane, isohexane, n-heptane, isoheptane, n-octane and isooctane, and preferably from propane and n-butane. Under certain conditions, it has been noticed that the other initial alkane(s) can react by hydrogenolysis with the hydrogen produced by the methane coupling reaction and can thus favourably shift the methane coupling reaction towards the formation of ethane. Such conditions can exist in particular when the process is carried out in the presence of a hydrogenolysis catalyst. This is particularly advantageous when the other optional initial alkane(s) are chosen from propane and n-butane, which, by hydrogenolysis, can produce in particular ethane.

The other optional initial alkane(s) can preferably be present with the methane in relatively low proportions, so that the ethane is produced in particular in a proportion of at least 65% by weight with respect to carbon-containing products formed (or in one of the other proportions mentioned above), that is to say with a high selectivity by weight for ethane, such as one of those mentioned above. Thus, according to the invention, methane can be used substantially as the only initial alkane, so that other initial alkane(s) can be used in an amount of less than $10^{-5}$ mol, preferably than $5 \times 10^{-6}$ mol, in particular than $10^{-6}$ mol, per mole of methane.

When the process of the invention is carried out in particular batchwise, the metal catalyst can be brought into contact with the methane in a molar ratio of the methane to the metal, Me, of the metal catalyst extending over a wide range, for example from 10:1 to $10^5$:1, preferably from 50:1 to $10^4$:1, in particular from 50:1 to $10^3$:1.

The process of the invention can be carried out in the presence of one or more inert agents, in particular liquid or gaseous inert agents, especially in the presence of one or more inert gases, such as nitrogen, helium or argon.

The process of the invention can be carried out batchwise or, preferably, continuously. It can be carried out in gas phase, in particular in a fluidized bed reactor and/or a reactor with a mechanically stirred bed, or in a stationary bed reactor or circulating bed reactor, in which reactor the bed can be formed essentially with the metal catalyst in a solid form, preferably of the metal catalyst supported on and grafted to a solid support, such as described subsequently. It is preferable to carry out the process of the invention continuously and in gas phase, in particular in which methane is introduced continuously into a reaction zone comprising the metal catalyst, so as to form a gas mixture comprising ethane, the gas mixture is continuously withdrawn from the reaction zone, the ethane produced is separated, at least partially and continuously, in the withdrawn gas mixture, from unreacted methane and optionally hydrogen formed, the ethane is thus recovered and, preferably, unreacted methane is returned to the reaction zone.

The process of the invention is advantageously carried out with a metal catalyst comprising at least one metal, Me, chosen from the lanthanides, the actinides and the metals from Groups 2 to 12, preferably 3 to 12, of the Periodic Table of the Elements. In particular, the process is carried out in the presence of a metal catalyst selected amongst metal catalysts suitable for converting methane into ethane with the above-mentioned selectivity for ethane. More particularly, the metal catalyst can be chosen from metal catalysts supported on and preferably grafted to a solid support. The metal catalyst can be also selected from metal hydrides, metal organic compounds and mixtures thereof, preferably containing the metal Me, and preferably supported on and in particular grafted to a solid support.

The term "metal catalyst supported on and grafted to a solid support" is generally understood to mean a metal catalyst comprising a solid support and at least one metal, preferably the metal Me, which is (chemically) attached to the solid support, in particular by at least a single or multiple bond, and in particular which is bonded directly to at least one of the essential elements (or constituents) of the solid support.

The metal, Me, present in the metal catalyst can be at least one metal chosen from the lanthanides, the actinides and the metals from Groups 2 to 12, preferably from Groups 3 to 12, in particular from the transition metals from Groups 3 to 11, and in particular from Groups 3 to 10, of the Periodic Table of the Elements. The metal, Me, can be in particular at least one metal chosen from yttrium, scandium, lanthanum, titanium, zirconium, hafnium, vanadium, niobium, tantalum, chromium, molybdenum, tungsten, rhenium, iron, ruthenium, cobalt, rhodium, nickel, iridium, palladium, platinum, cerium and neodymium. It can preferably be chosen from yttrium, titanium, zirconium, hafnium, vanadium, niobium, tantalum, chromium, molybdenum, tungsten, ruthenium, rhodium and platinum and more particularly from yttrium, vanadium, niobium, tantalum, chromium, molybdenum, tungsten, ruthenium, rhodium and platinum.

The metal catalyst can be preferably chosen from metal catalysts supported on and grafted to a solid support, comprising a solid support and one or more metals, Me, which are identical or different and which are in particular (chemically) attached to the solid support, especially by single or multiple bonds. The metal, Me, atom can, in addition, advantageously be bonded to at least one hydrogen atom and/or to at least one hydrocarbon radical.

In the case where the metal, Me, grafted to a solid support is bonded to at least one hydrogen atom, the metal catalyst can be chosen from supported and grafted metal catalysts comprising a solid support to which is grafted at least one metal hydride of the metal Me.

In the case where the metal, Me, grafted to a solid support is bonded to at least one hydrocarbon radical, the metal catalyst can be chosen from supported and grafted metal catalysts comprising a solid support to which is grafted at least one organometallic compound of the metal Me.

The metal catalyst can also be advantageously chosen from supported and grafted metal catalysts comprising a solid support to which are grafted at least two types of metal Me, one in a form (A) of a metal compound where the metal, Me, is bonded to at least one hydrogen atom and/or to at least one hydrocarbon radical, and the other in a form (B) of a metal compound where the metal, Me, is bonded solely to the solid support and optionally to at least one other element which is neither a hydrogen atom nor a hydrocarbon radical. In each of the forms (A) and (B), the metal catalyst can comprise one or more different metals, Me. The metal Me present in the form (A) can be identical to or different from that present in the form (B). When the forms (A) and (B) coexist in the metal catalyst, the degree of oxidation of the metals Me present in the form (A) can be identical to or different from that of the metals Me present in the form (B).

The solid support can be any solid support, preferably chosen from inorganic solid supports, in particular comprising essentially atoms M and X which are different from one another and which are generally bonded to one another by single or multiple bonds, so as to form in particular the molecular structure of the solid support. The term "support comprising essentially atoms M and X" is generally understood to mean a support which comprises the atoms M and X as predominant constituents and which can additionally comprise one or more other atoms capable of modifying the structure of the support.

The atom M of the solid support can be at least one of the elements chosen from the lanthanides, the actinides and the elements from Groups 2 to 15 of the Periodic Table of the Elements. The atom M of the solid support can be identical to or different from the metal Me. The atom M can be at least one of the elements chosen in particular from magnesium, titanium, zirconium, cerium, vanadium, niobium, tantalum, chromium, molybdenum, tungsten, boron, aluminium, gallium, silicon, germanium, phosphorus and bismuth. The atom M of the solid support is preferably at least one of the elements chosen from the lanthanides, the actinides and the elements from Groups 2 to 6 and from Groups 13 to 15 of the Periodic Table of the Elements, in particular from silicon, aluminium and phosphorus.

The atom X of the solid support, which is different from the atom M, can be chosen from at least one of the elements from Groups 15 and 16 of the Periodic Table of the Elements, it being possible for the element to be alone or itself optionally bonded to another atom or to a group of atoms. In the case where the atom X of the solid support is chosen in particular from at least one of the elements from Group 15, it can optionally be bonded to another atom or to a group of atoms chosen, for example, from a hydrogen atom, a halogen atom, in particular a fluorine, chlorine or bromine atom, a saturated or unsaturated hydrocarbon radical, a hydroxyl group of formula (HO—), a hydrosulphide group of formula (HS—), alkoxide groups, thiolate groups, silylated (or silane) groups or organosilylated (or organosilane) groups. Preferably, the atom X of the solid support is at least one of the elements chosen from oxygen, sulphur and nitrogen and more particularly from oxygen and sulphur.

The atoms M and X, which generally represent the essential elements of the solid support, can in particular be bonded to one another via single or double bonds. In a preferred alternative form, the solid support can be chosen from metal oxides, refractory oxides, molecular sieves, sulphated metal oxides, sulphated refractory oxides, metal sulphides, refractory sulphides, sulphided metal oxides, sulphided refractory oxides and azides.

In particular, the solid support may be chosen from oxides, sulphides and azides, in particular M, and mixtures of two or three oxides, sulphides and/or azides. More particularly, the solid support can be an oxide, in particular an oxide of M, and can be chosen from simple or mixed oxides, in particular simple or mixed oxides of M, or mixtures of oxides, in particular mixtures of oxides M. The solid support can, for example, be chosen from metal oxides, refractory oxides and molecular sieves, in particular from silica, alumina, silicoaluminates, aluminium silicates, simple or modified by other metals, zeolites, clays, titanium oxide, cerium oxide, magnesium oxide, niobium oxide, tantalum oxide and zirconium oxide. The solid support can also be a metal oxide or a refractory oxide, optionally modified by an acid, and can optionally comprise in particular an atom M bonded to at least two atoms X which are different from one another, for example the oxygen atom and the sulphur atom. Thus, the solid support can be chosen from sulphated metal oxides or sulphated refractory oxides, for example a sulphated alumina or a sulphated zirconia. The solid support can also be chosen from metal sulphides, refractory sulphides, sulphided metal oxides and sulphided refractory oxides, for example a molybdenum sulphide, a tungsten sulphide or a sulphided alumina. The solid support can also be chosen from azides, in particular boron azide.

The essential constituents of the solid support are preferably the atoms M and X described above. In addition, the solid support has the advantage of generally exhibiting, at the surface, atoms X capable of forming part of the coordination sphere of the metal, Me, of the metal catalyst, in particular when the catalyst is chosen from metal compounds supported on and grafted to a solid support. Thus, at the surface of the support, the atom N which is bonded to at least one metal atom, Me, can advantageously be additionally bonded to at least one atom M. The bonds between X and M and those between X and Me can be single or double bonds.

In the case of a metal catalyst supported on and grafted to a support, the metal, Me, present in particular in the form (A) can be bonded, on the one hand, to the support, in particular to at least one atom constituting the support, preferably the atom X of the support as described above, in particular by a single or double bond, and, on the other hand, to at least one hydrogen atom and/or to at least one hydrocarbon radical, R, in particular by a carbon-metal single, double or triple bond. The hydrocarbon radical, R, can be saturated or unsaturated, can have from 1 to 20, preferably from 1 to 10, carbon atoms and can be chosen from alkyl, alkylidene or alkylidyne radicals, in particular $C_1$ to $C_{10}$ radicals, preferably $C_1$ radicals, aryl radicals, in particular $C_6$ to $C_{10}$ radicals, and aralkyl, aralkylidene or aralkylidyne radicals, in particular $C_7$ to $C_{14}$ radicals.

In the case of a metal catalyst supported on and grafted to a support, the metal, Me, present in particular in the form (A), can be bonded to the hydrocarbon radical, R, via one or more carbon-metal single, double or triple bonds. It can be a matter of a carbon-metal single bond, in particular of the σ type: in this case, the hydrocarbon radical, R, can be an alkyl radical, in particular a linear or branched radical, for example a $C_1$ to $C_{10}$, preferably $C_1$, radical, or an aryl radical, for example the phenyl radical, or an aralkyl radical, for example the benzyl radical. The term "alkyl radical" is generally understood to mean a monovalent aliphatic radical resulting from the removal of a hydrogen atom from the molecule of an alkane or of an alkene or of an alkyne, for example the methyl, ethyl, propyl, neopentyl, allyl or ethynyl radical. The methyl radical is preferred.

It can also be a matter of a carbon-metal double bond, in particular of the π type: in this case, the hydrocarbon radical, R, can be an alkylidene radical, in particular a linear or branched radical, for example $C_1$ to $C_{10}$, preferably $C_1$, radical, or an aralkylidene radical, for example a $C_7$ to $C_{14}$ radical. The term "alkylidene radical" is generally understood to mean a bivalent aliphatic radical originating from the removal of two hydrogen atoms from the same carbon of the molecule of an alkane or of an alkene or of an alkyne, for example the methylidene, ethylidene, propylidene, neopentylidene or allylidene radical. The metlhylidene radical is preferred. The term "aralkylidene radical" is generally understood to mean a bivalent aliphatic radical originating from the removal of two hydrogen atoms from the same carbon of an alkyl, alkenyl or alkynyl linking unit of an aromatic hydrocarbon.

It can also be a matter of a carbon-metal triple bond: in this case, the hydrocarbon radical, R, can be an alkylidyne radical, in particular a linear or branched radical, for example a $C_1$ to $C_{10}$, preferably $C_1$, radical, or an aralkylidyne radical, for example a $C_7$ to $C_{14}$ radical. The term "alkylidyne radical" is generally understood to mean a trivalent aliphatic radical originating from the removal of three hydrogen atoms from the same carbon of the molecule of an alkane or of an alkene or of an alkyne, for example the metilylidyne, ethylidyne, propylidyne, neopentylidyne or allylidyne radical. The methylidyne radical is preferred. The term "aralkylidyne radical" is generally understood to mean a trivalent aliphatic radical originating from the removable of three hydrogen atoms from the same carbon of an alkyl, alkenyl or alkynyl linking unit of an aromatic hydrocarbon.

The metal catalyst can advantageously be chosen from metal catalysts supported on and grafted to a solid support comprising the metal, Me, present in both forms (A) and (B). Such a metal catalyst has the advantage of exhibiting a very high catalytic activity in the reaction for producing ethane from methane or for the conversion of methane into ethane.

The form (A) of the metal catalyst is that described above. In the form (B), the metal, Me, is preferably bonded solely to the support, in particular to one or more atoms constituting the essential elements of the support, in particular to one or more atoms X of the support such as are described above, for example by single or double bonds.

In the form (B), the metal, Me, can optionally be bonded, in addition to the support, to at least one other element which is neither a hydrogen atom nor a hydrocarbon radical. The other element bonded to the metal Me can, for example, be at least one of the elements from Groups 15 to 17 of the Periodic Table of the Elements, which element can be alone or itself bonded to at least one hydrogen atom and/or to at least one hydrocarbon radical and/or to at least one silylated (or silane) or organosilylated (or organosilane) group. In particular, the metal, Me, present in the form (B) can also be bonded, in addition to the support, to at least one atom of the elements chosen from oxygen, sulphur, nitrogen and halogens, in particular fluorine, chlorine or bromine. Thus, for example, the metal, Me, can be bonded, via a single bond, to one or more halogen atoms, in particular fluorine, chlorine or bromine. It can also be bonded, via a double bond, to one or more oxygen or sulphur atoms, in particular in the form of a metal oxide or sulphide. It can also be bonded, via a single bond, to at least one oxygen or sulphur atom itself bonded to a hydrogen atom or to a saturated or unsaturated hydrocarbon radical, in particular a $C_1$ to $C_{20}$, preferably $C_1$ to $C_{10}$, radical, for example in the form of a hydroxide, of a hydrosulphide, of an alkoxide or of a thiolate. It can also be bonded, via a single bond, to a silylated or organosilylated group. It can also be bonded, via a single bond, to an amido (or amide) group, for example of formulae ($H_2N-$), (HRN—) or (RR'N—) in which R and R', which are identical or different, represent saturated or unsaturated hydrocarbon radicals, in particular $C_1$ to $C_{20}$, preferably $C_1$ to $C_{10}$, radicals or silylated or organosilylated groups or else can be bonded, via a double bond, to an imido (or imide) group, for example of formula (HN=), or, via a triple bond, to a nitrido (or azide) group, for example of formula (N≡).

It is preferable to use metal catalysts supported on or grafted to a solid support in which the metal, Me, grafted to the support exists simultaneously in both forms (A) and (B), as these catalysts advantageously exhibit a very high catalytic activity in methane coupling or homologation reactions. This is in particular the case when, per 100 mol of the metal Me grafted to the support, the metal catalyst comprises:

(a) from 5 to 95 mol, preferably from 10 to 90 mol, in particular from 20 to 90 mol, especially from 25 to 90 mol, or more particularly from 30 to 90 mol, of the metal Me in the form (A), and (b) from 95 to 5 mol, preferably from 90 to 10 mol, in particular from 80 to 10 mol, especially from 75 to 10 mol, or more particularly from 70 to 10 mol, of the metal Me in the form (B).

The metal catalysts described above can be prepared in various ways. A first process for the preparation of a metal catalyst supported on and grafted to a solid support can comprise the following stages:

(a) an organometallic precursor (P) comprising the metal Me bonded to at least one hydrocarbon ligand is grafted to the solid support, and (b) the solid product resulting from stage (a) is treated with hydrogen or a reducing agent capable of forming a metal Me-hydrogen bond, preferably by hydrogenolysis of the hydrocarbon ligands, at a temperature in particular at most equal to the temperature T1 at which the catalyst is formed solely in the form (A) as defined above.

The temperature of stage (b) is chosen in particular so that it is at most equal to the temperature T1 where only the form (A) of the catalyst is formed, that is to say where only the metal hydride is formed. The temperature of stage (b) can in particular be chosen within a range from 50 to 160° C., preferably from 100 to 150° C. Stage (b) can take place under an absolute pressure of $10^{-3}$ to 10 MPa and for a period of time which can range from 1 to 24 hours, preferably from 5 to 20 hours.

A second process for the preparation of a metal catalyst can comprise the following stages:
- (a) an organometallic precursor (P) comprising the metal Me bonded to at least one hydrocarbon ligand is grafted to the solid support, and
- (b) the solid product resulting from stage (a) is treated with hydrogen or a reducing agent capable of forming a metal Me-hydrogen bond, preferably by hydrogenolysis of the hydrocarbon ligands, at a temperature greater than the temperature T1 at which the catalyst is formed solely in the form (A) and less than the temperature T2 at which the catalyst is formed solely in the form (B), the forms (A) and (B) being those described above.

The temperature of stage (b) is chosen in particular so that it is greater than the temperature T1 where only the form (A) is formed. It can in particular be at least 10° C., preferably at least 20° C., in particular at least 30° C. or even at least 50° C. greater than the temperature T1. It is in addition chosen in particular so that it is less than the temperature T2 where only the form (B) is formed. It can in particular be at least 10° C., preferably at least 20° C., in particular at least 30° C. or even at least 50° C. less than the temperature T2. The temperature of stage (b) can, for example, be chosen within a range from 165° C. to 450° C., preferably from 170 to 430° C., in particular from 180 to 390° C., in particular from 190 to 350° C. or from 200 to 320° C. Stage (b) can take place under an absolute pressure of $10^{-3}$ to 10 MPa and for a period of time which can range from 1 to 24 hours, preferably from 5 to 20 hours.

A third process for the preparation of a metal catalyst can comprise the following stages:
- (a) an organometallic precursor (P) comprising the metal Me bonded to at least one hydrocarbon ligand is grafted to the solid support, then
- (b) the solid product resulting from stage (a) is treated with hydrogen or a reducing agent capable of forming a metal Me-hydrogen bond, preferably by complete hydrogenolysis of the hydrocarbon ligands, at a temperature in particular at most equal to the temperature T1 at which the catalyst is formed solely in the form (A) as defined above, so as to form a metal hydride in the form (A), and
- (c) the solid product resulting from stage (b) is heat-treated, preferably in the presence of hydrogen or of a reducing agent, at a temperature greater than the temperature of stage (b) and less than the temperature T2 at which the catalyst is formed solely in the form (B) as defined above.

Stage (b) of the process can be carried out under the same conditions, in particular of temperature, as those of stage (b) of the first preparation process. Stage (c) can be carried out at a temperature, under a pressure and for a period of time equivalent to those described in stage (b) of the second preparation process.

A fourth process for the preparation of a metal catalyst can comprise the following stages:
- (a) an organometallic precursor (P) comprising the metal Me bonded to at least one hydrocarbon ligand is grafted to the solid support comprising functional groups capable of grafting the precursor (P) by bringing the precursor (P) into contact with the solid support so as to graft the precursor (P) to the support by reaction of (P) with a portion of the functional groups of the support, preferably from 5 to 95% of the functional groups of the support, then
- (b) the solid product resulting from stage (a) is heat-treated, preferably in the presence of hydrogen or of a reducing agent, at a temperature equal to or greater than the temperature T2 at which the catalyst is formed solely in the form (B) as defined above, then
- (c) an organometallic precursor (P'), identical to or different from (P), comprising the metal Me bonded to at least one hydrocarbon ligand, the metal Me and the ligand being identical to or different from those of (P), is grafted to the solid product resulting from stage (b) by bringing the precursor (P') into contact with the solid product resulting from stage (b) so as to graft the precursor (P') to the support by reaction of (P') with the functional groups remaining in the support, and optionally
- (d) the solid product resulting from stage (c) is treated with hydrogen or a reducing agent capable of forming metal Me-hydrogen bonds, preferably by complete hydrogenolysis of the hydrocarbon ligands of the grafted precursor (P'), at a temperature in particular at most equal to the temperature T1 at which the catalyst is formed solely in the form (A) as defined above.

Stage (b) of the process can be carried out at a temperature such that most, preferably all, of the precursor (P) grafted to the support is converted to metal compound in the form (B). The temperature during stage (b) can be chosen within a range from 460° C., preferably from 480° C., in particular from 500° C., up to a temperature below the sintering temperature of the support. Stage (d) is optional and can be carried out at a temperature equivalent to that of stage (b) of the first preparation process.

A fifth process for the preparation of a metal catalyst can comprise the following stages:
- (a) an organometallic precursor is grafted to the solid support under the same conditions as in stage (a) of the preceding preparation process, then
- (b) the solid product resulting from stage (a) is treated under the same conditions as in stage (b) of the preceding preparation process, then
- (c) the solid product resulting from stage (b) is brought into contact with at least one compound Y capable of reacting with the metal Me of the form (A) and/or (B), prepared above, the contacting operation preferably being followed by removable of the unreacted compound Y and/or by a heat treatment at a temperature below the sintering temperature of the support, then
- (d) an organometallic precursor (P'), identical to or different from (P), comprising the metal Me bonded to at least one hydrocarbon ligand, the metal Me and the ligand being identical [lacuna] or different from those of (P), is grafted to the solid product resulting from stage (c) by bringing the precursor (P') into contact with the product resulting from stage (c) so as to graft the precursor (P') to the support by reaction of (P') with the functional groups remaining in the support, and optionally
- (e) the solid product resulting from stage (d) is treated with hydrogen or a reducing agent capable of forming metal Me-hydrogen bonds, preferably by complete hydrogenolysis of the hydrocarbon ligands of the grafted precursor (P'), at a temperature in particular at most equal to the temperature T1 at which the catalyst is formed solely in the form (A) as defined above.

Stage (b) of the process can be carried out at a temperature equivalent to that of stage (b) of the fourth preparation process. In stage (c), the compound Y can be chosen from molecular oxygen, water, hydrogen sulphide, ammonia, an alcohol, in particular a $C_1$ to $C_{20}$, preferably $C_1$ to $C_{10}$, alcohol, a thiol, in particular a $C_1$ to $C_{20}$, preferably $C_1$ to $C_{10}$, thiol, a primary or secondary $C_1$ to $C_{20}$, preferably $C_1$ to $C_{10}$, amine, a molecular halogen, in particular molecular fluorine, chlorine or bromine, and a hydrogen halide, for example of formula HF, HCl or HBr. The heat treatment optionally carried out at the end of stage (c) can be carried out at a temperature ranging from 25 to 500° C. Stage (e) is optional and can be carried out at a temperature equivalent to that of stage (b) of the first preparation process.

In the processes for the preparation of a supported and grafted metal catalyst such as are described above, the operation of grafting to a solid support employs at least one organometallic precursor (P) or (P') comprising the metal Me bonded to at least one hydrocarbon ligand. The precursor can correspond to the general formula:

$$MeR'_a \quad (2)$$

in which Me has the same definition as above, R' represents one or more identical or different and saturated or unsaturated hydrocarbon ligands, in particular aliphatic or alicyclic ligands, in particular $C_1$ to $C_{20}$, preferably $C_1$ to $C_{10}$, ligands, for example having the same definition as that given above for the hydrocarbon radical, R, of the metal catalyst, and a is an integer equal to the degree of oxidation of the metal Me. The radical R' can be chosen from alkyl, alkylidene, alkylidyne, aryl, aralkyl, aralkylidene and aralkylidyne radicals. The metal Me can be bonded to one or more carbons of the hydrocarbonaceous ligands, R', in particular via carbonmetal single, double or triple bonds, such as those connecting the metal Me to the hydrocarbon radical, R, in the catalyst.

In the processes for the preparation of a supported and grafted metal catalyst such as are described above, the solid support is preferably subjected beforehand to a dehydration and/or dehydroxylation heat treatment, in particular at a temperature below the sintering temperature of the support, preferably at a temperature ranging from 200 to 1000° C., preferably from 300 to 800° C., for a period of time which can range from 1 to 48 hours, preferably from 5 to 24 hours. The temperature and the duration can be chosen so as to create and/or to allow to remain, in the support and at predetermined concentrations, functional groups capable of grafting by reaction the precursor (P) or (P'). Mention may be made, among functional groups known for the supports, of groups of formulae XH in which H represents a hydrogen atom and X corresponds to the same definition as given above for the support and in particular can represent an atom chosen from oxygen, sulphur and nitrogen. The most well-known functional group is the hydroxyl group.

The grafting operation can generally be carried out by sublimation or by bringing the precursor into contact in a liquid medium or in solution. In the case of a sublimation, the precursor, used in the solid state, can be heated under vacuum and the temperature and pressure conditions which provide for its sublimation and its migration in the vapour state onto the support. The sublimation can be carried out at a temperature ranging from 20 to 300° C., in particular from 50 to 150° C., under vacuum.

A grafting can also be carried out by carrying out the contacting operation in a liquid medium or solution. In this case, the precursor can be dissolved in an organic solvent, such as pentane or ethyl ether, so as to form a homogeneous solution, and the support can subsequently be suspended in the solution comprising the precursor or by any other method which provides for contact between the support and the precursor. The contacting operation can be carried out at ambient temperature (20° C.) or more generally at a temperature ranging from −80° C. to +150° C., under an inert atmosphere, such as nitrogen. If only a portion of the precursor has become attached to the support, the excess can be removed by washing or reverse sublimation.

The process of the present invention makes it possible to carry out a conversion of methane by a methane coupling or homologation reaction with an extremely high selectivity by weight for ethane with respect to carbon-containing products formed. The advantage of this process is that of being able to rapidly recover and isolate the ethane produced, simply by separating the ethane from unreacted methane and hydrogen formed. The ethane, thus recovered and isolated, can be employed in processes for enhancing the value of ethane, for example in dehydrogenation, catalytic cracking or thermal cracking processes, optionally in the presence of steam, so as to selectively manufacture in particular olefins, such as ethylene.

The following examples illustrate the present invention.

EXAMPLE 1

Preparation of a Tantalum Catalyst

A tantalum catalyst supported on and grafted to silica was prepared in the following way.

In a first step, 5 g of a silica dehydrated and treated at 500° C. beforehand and then 20 ml of an n-pentane solution comprising 800 mg (1.72 millimol of tantalum) of tris(neopentyl) neopentylidenetantalum, used as precursor and corresponding to the general formula:

$$Ta[-CH_2-C(CH_3)_3]_3[=CH-C(CH_3)_3] \quad (3)$$

were introduced under an argon atmosphere into a glass reactor. The precursor was grafted at 25° C. to the silica, in particular by reaction with the hydroxyl groups of the silica. The excess precursor which had not reacted was removed by washing with n-pentane. The resulting solid compound, which constituted the organometallic compound grafted to the silica and which corresponded to the general formula:

$$(Si-O)_{1.35}Ta[=CH-C(CH_3)_3][-CH_2-C(CH_3)_3]_{1.65} \quad (4)$$

was then dried under vacuum.

In a second stage, the tantalum compound, thus supported on and grafted to the silica, was subsequently treated under an atmosphere of 80 kPa of hydrogen at a temperature of 250° C. for 15 hours. By hydrogenolysis of the neopentyl and neopentylidene ligands, a tantalum catalyst supported on and grafted to silica was formed which, per 100 parts by moles of tantalum, comprised:

72 parts by moles of a tantalum hydride grafted to the silica in the form (A) corresponding to the general formula:

$$[(silica\ support)-Si-O]_2-Ta-H \quad (5)$$

and 28 parts by moles of a tantalum compound grafted to the silica in the form (B) corresponding to the general formula:

[(silica support)-Si—O]$_3$—Ta     (6)

EXAMPLE 2

Methane Coupling Reaction

Conversion of methane by a coupling reaction, converting methane essentially to ethane, was carried out in the following way.

Methane was passed continuously according to a flow rate of 3 Sml/min (i.e. $1.33 \times 10^{-4}$ mol of methane per minute), under a total absolute pressure of 5 MPa, through a reactor with a capacity of 5 ml which was heated at 250° C. and which comprised 300 mg of the tantalum catalyst prepared in Example 1 (59.3 micromol of tantalum in the form (A)).

Bringing methane into contact with the tantalum catalyst resulted in the formation of ethane and hydrogen, according to the methane coupling reaction written according to the following equation:

$$2CH_4 \rightarrow C_2H_6 + H_2 \quad (1)$$

It was observed that the conversion of the methane exhibited a selectivity by weight for ethane with respect to carbon-containing products formed of greater than 99.9%. In particular, no detectable trace was found of alkene or alkyne formed, such as ethylene or acetylene, or of aromatic compounds, such as benzene, of carbon monoxide or of carbon dioxide.

During the reaction, the instantaneous concentrations of hydrogen, methane, ethane and carbon-containing products formed in the conversion were regularly measured, and the instantaneous molar ratios of ethane formed and hydrogen formed with respect to the tantalum of the catalyst (respectively $[C_2]_{ins}/[Ta]$ and $[H_2]_{ins}/[Ta]$), the cumulative molar ratios of ethane formed and hydrogen formed with respect to the tantalum of the catalyst (respectively $[C_2]_{cum}/[Ta]$ and $[H_2]_{cum}/[Ta]$) and the instantaneous percentage of conversion of the methane (% $C_1$ conv) were calculated. The results of these measurements and calculations were collated in Table 1.

TABLE 1

| Time (min) | $[C_2]_{ins}/[Ta]$ | $[H_2]_{ins}/[Ta]$ | % $C_1$ conv. | $[C_2]_{cum}/[Ta]$ | $[H_2]_{cum}/[Ta]$ |
|---|---|---|---|---|---|
| 1 500 | $8.0 \times 10^{-5}$ | $1.5 \times 10^{-4}$ | 0.028 | 0.25 | 0.75 |
| 3 000 | $7.5 \times 10^{-5}$ | $1.05 \times 10^{-4}$ | 0.026 | 0.55 | 1.3 |
| 6 000 | $6.0 \times 10^{-5}$ | $7.5 \times 10^{-5}$ | 0.021 | 1.1 | 2.05 |
| 8 500 | $5.5 \times 10^{-5}$ | $6.0 \times 10^{-5}$ | 0.018 | 1.5 | 2.5 |

In addition, Table 1 shows that the number of moles of methane which had reacted per mole of tantalum, after reacting for 8 500 minutes, was equal to approximately 3.

EXAMPLE 3

Methane Coupling Reaction

Conversion of methane to ethane, by a coupling reaction of the latter, was carried out exactly as in Example 2, except that the reactor was heated at different temperatures (instead of 250° C.), namely at 300° C., 375° C. and 475° C. respectively in Runs A, B and C.

In each run, the coupling reaction was carried out during 6500 minutes, and at that time, the instantaneous concentrations of methane, ethane and carbon-containing products formed in the conversion were measured, and the instantaneous percentage of conversion of the methane (% $C_1$ conv), the number of moles of methane having reacting per mole of tantalum ($C_1$ reacted/Ta) and the selectivity by weight for ethane ($C_2H_6$ selectivity) were calculated. The results of these measurements and calculations were collated in Table 2.

TABLE 2

| Run | Temperature (° C.) | % $C_1$ conv | $C_1$ reacted/Ta | $C_2H_6$ selectivity (%) |
|---|---|---|---|---|
| A | 300 | 0.054 | 6.2 | 99.7 |
| B | 375 | 0.102 | 14.3 | 99.0 |
| C | 475 | 0.227 | 33 | 96.1 |

Table 2 shows that the number of moles of methane having reacted per mole of tantalum had greatly increased by a factor of about 5.3 between 300° C. and 475° C., while the slectivity by weight for ethane had only slightly decreased from 99.7 to 96.1%.

EXAMPLE 4

Preparation of a Tungsten Catalyst

A tungsten catalyst supported on and grafted to silica was prepared exactly as in Example 1, except that, in the first stage, instead of using a solution of tris(neopentyl)neopentylidenetantalum in n-pentane, use was made of a solution of tris(neopentyl)neopentylidynetungsten in n-pentane, corresponding to the general formula:

$$W[—CH_2—C(CH_3)_3]_3[\equiv C—C(CH_3)_3] \quad (7)$$

and that, in the second stage, instead of carrying out the hydrogenolysis at 250° C., it was carried out at 150° C. A tungsten catalyst supported on silica was thus obtained essentially in the form (A) of a tungsten hydride.

EXAMPLE 5

Methane Couplings Reaction

Conversion of methane to ethane, by a coupling reaction of the latter, was carried out as in Example 2, except that, instead of using the tantalum catalyst prepared in Example 1, the tungsten catalyst prepared above in Example 4 was used.

Under these conditions, it was observed that the methane coupling reaction resulted in the formation of ethane and hydrogen with a selectivity by weight for ethane with respect to carbon-containing products formed of greater than 99.9%. In particular, no detectable trace was found of alkene or alkyne formed, such as ethylene or acetylene, or of aromatic compound, such as benzene, of carbon monoxide or of carbon dioxide.

The invention claimed is:

1. A process for producing ethane comprising bringing a stream consisting essentially of methane into contact with a metal catalyst selected from the group consisting of metal hydrides, metal organic compounds and mixtures thereof at the operating conditions for methane conversion.

2. The process according to claim 1, wherein the metal catalyst comprises at least one metal selected from the group consisting of lanthanides, the actinides and the metals from Groups 2 to 12 of the Periodic Table of the Elements.

3. A process for the conversion of methane to carbon-containing products comprising bringing a stream consisting essentially of methane into contact with a metal catalyst comprising at least one metal selected from the group consisting of lanthanides, the actinides and the metals from Groups 2 to 12 of the Periodic Table of the Elements, so as to produce ethane in a proportion of at least 65% by weight with respect to carbon-containing products formed in the process.

4. The process according to claim 3, wherein the ethane is produced in a proportion of at least 70% by weight with respect to carbon-containing products formed in the process.

5. The process according to claim 3 or 4, wherein the metal catalyst is selected from the group consisting of metal hydrides, metal organic compounds and mixtures thereof.

6. The process according claim 1 or 3, wherein the process is carried out under conditions involving a non-oxidative coupling of methane.

7. The process according to claim 1 or 3, wherein the process is a single-stage process.

8. The process according to claim 1 or 3, wherein the process is carried out with operating conditions maintained substantially constant during the ethane production.

9. The process according to claim 1 or 3, wherein the process is carried out under a total absolute pressure ranging from $10^{-3}$ to 100 MPa.

10. The process according to claim 1 or 3, wherein the process is carried out at a temperature ranging from −30° C. to +800° C.

11. The process according to claim 1 or 3, wherein the process is carried out in the presence of one or more inert agents.

12. The process according to claim 1 or 3, wherein the metal catalyst is supported on a solid support.

13. The process according to claim 12, wherein the solid support is selected from the group consisting of metal oxides, refractory oxides, molecular sieves, sulphated metal oxides, sulphated refractory oxides, metal sulphides, refractory sulphides, sulphided metal oxides, sulphided refractory oxides and azides.

14. The process according to claim 1 or 3, wherein the metal of the metal catalyst is at least one metal selected from the group consisting of yttrium, scandium, lanthanum, titanium, zirconium, hafnium, vanadium, niobium, tantalum, chromium, molybdenum, tungsten, rhenium, iron, ruthenium, cobalt, rhodium, iridium, nickel, palladium, platinum, cerium and neodymium.

15. The process according to claim 14, wherein the metal is at least one metal selected from the group consisting of yttrium, titanium, zirconium, hafnium, vanadium, niobium, tantalum, chromium, molybdenum, tungsten, ruthenium, rhodium and platinum.

16. The process according to claim 15, wherein the metal is at least one metal selected from the group consisting of yttrium, vanadium, niobium, tantalum, chromium, molybdenum, tungsten, ruthenium, rhodium and platinum.

17. The process according to claim 1 or 3, wherein the process is carried out in the gas phase in a reactor.

18. The process according to claim 17, wherein the metal catalyst is used in a solid form, essentially forming the bed of the reactor.

19. The process according to claim 1 or 3, wherein the process comprises adding the methane to the metal catalyst, or adding the metal catalyst to the methane, or simultaneously mixing the methane and the metal catalyst.

* * * * *